United States Patent [19]

Stavropoulos et al.

[11] 4,024,021

[45] May 17, 1977

[54] DETERMINATION OF GLUTAMATE AND GLUTAMIC TRANSAMINASES

[75] Inventors: William S. Stavropoulos, Carmel; Kenneth J. Acuff, Indianapolis, both of Ind.

[73] Assignee: The Dow Chemical Company, Midland, Mich.

[22] Filed: May 9, 1975

[21] Appl. No.: 575,879

Related U.S. Application Data

[63] Continuation of Ser. No. 380,810, July 19, 1973, abandoned.

[52] U.S. Cl. .......................... 195/103.5 R; 195/63; 195/99
[51] Int. Cl.² ........................................ G01N 31/14
[58] Field of Search ................ 195/99, 103.5 R, 68, 195/63

[56] References Cited

UNITED STATES PATENTS

| | | | |
|---|---|---|---|
| 3,069,330 | 12/1962 | Babson | 195/103.5 R |
| 3,527,332 | 9/1970 | Deutsch | 195/103 5 R |
| 3,546,074 | 12/1970 | Deutsch | 195/103.5 R |
| 3,764,478 | 10/1973 | Bergmeyer et al. | 195/99 |

OTHER PUBLICATIONS

Lippi et al., A New Colorimetric Ultramicromethod for Serum Glutamic–Oxalacetic and Glutamic–Pyluvic Transaminase Determination, Clinica Chimica Acta., vol. 28, 1970 (pp. 431–437).

*Primary Examiner*—David M. Naff
*Attorney, Agent, or Firm*—Maynard R. Johnson

[57] ABSTRACT

Glutamate and glutamic transaminases are determined by mixing a substrate-reagent composition that is essentially free of ammonia or ammonium ions with a specimen to be analyzed, incubating the resulting mixture for less than about 15 minutes, terminating incubation and measuring a color produced.

3 Claims, No Drawings

DETERMINATION OF GLUTAMATE AND GLUTAMIC TRANSAMINASES

This is a continuation, of application Ser. No. 380,810 filed July 19, 1973, now abandoned.

BACKGROUND OF THE INVENTION

Colorimetric determinations of glutamic transaminases in biological fluids are carried out by various methods in many laboratories. The value of such determinations as an aid in diagnosis of myocardial infarction and necrosis of hepatic cells is well established. Reitman and Frankel, Am. J. Clin. Pathol. 28, 56 (1957). The enzymes of primary significance are glutamic oxalacetic transaminase (GOT), which catalyzes the reaction L-Aspartate + α-Oxoglutarate ⇌ Oxalacetate + L-Glutamate and the enzyme glutamic pyruvic transaminase (GPT) which catalyzes the reaction L-Alanine + α-Oxoglutarate ⇌ Pyruvate + L-Glutamate The methods are based on the enzyme-catalyzed transamination of a substrate containing α-oxoglutarate and an appropriate amino acid to produce glutamate and another acid, pyruvate in the case of GPT and oxalacetate in the case of GOT.

Some colorimetric methods are based on a color reaction involving the acid produced. More recently, a method has been described in which glutamate produced in the transamination reaction is dehydrogenated, using the enzyme glutamate dehydrogenase, (G1DH) in aqueousl ammonium sulfate and the coenzyme oxidized nicotinamideadenine dinucleotide (NAD), to form α-oxoglutarate, ammonia and reduced nicotinamide-adenine dinucleotide (NADH), Glutamate +H$_2$O+NAD  α-Oxoglutarate +NH$_3$+NADH. The NADH produced is reacted with a colorless tetrazolium dye, 2-p-iodophenyl-3-nitrophenyl-5-phenyltetrazolium chloride (INT) with the aid of an electron carrier, such as N-methyl phenazonium methosulfate (PMS) to form a colored dye (INT formazan), in a reaction catalyzed by the electron carrier, as follows:

NADA + INT $\xrightarrow{PMS}$ NAD + INT formazan

The intensity of the color formed in then measured to give a measurement of the transaminase activity, Lippi and Guidi, Clin. Chim. Acta, 28, 431 (1970).

The transaminase determination is usually performed on a biological fluid such as serum in the differential diagnoses of liver and heart disease. A predetermined volume of sample fluid is mixed with a predetermined volume of a substrate composition buffered to a pH of about 7.4 and containing α-oxoglutarate and either aspartic acid (for GOT) or alanine (for GPT). A color developer solution or solutions containing the GlDH, INT and NAD are also employed. The substrate, sample and color developer are mixed in a container such as a colorimeter color developer cuvette or test tube. The mixture is incubated, typically in a water bath or heating block at 37° C. for a predetermined period of time, about 45–60 minutes. The incubation is terminated by addition of acid and the intensity of the resulting color is measured photometrically in a spectrophotometer or colorimeter at a wavelength from 490 to 550 nanometers, and compared with a control serum, calibration curve or the like.

BRIEF SUMMARY OF THE INVENTION

This invention relates to an improvement in glutamate determinations by the reaction of NADH with tetrazolium indicators and includes improved glutamic transaminase determinations by means of the coupling of the transamination through glutamate dehydrogenase and NAD, to the color reaction of NADH with tetrazolium salt indicators. The invention provides a reagent - substrate composition comprising a transaminase substrate, NAD, glutamate dehydrogenase, and the tetrazolium color reagent in a single, liquid composition. In the method of the invention, the substrate reagent composition is mixed with a specimen to the analyzed for transaminase activity or for glutamate and incubated therewith for relatively brief periods, such as from about 5 or less to about 15 minutes, prior to terminating the incubation with acid and measuring color.

The reagent - substrate composition and the method of the invention provide several advantages in the determination of glutamate and of glutamic transaminase enzymes. It can be prepared in large quantities, with the advantages of ease in measuring amounts of ingredients, standardization, and elimination of mixing operations from the actual determination. The incubation time required for determination of transaminase by the invention is much less than the time required for determination by prior art methods, e.g., the determination can be carried in a ten minute incubation time as opposed to periods of 45 minutes. The method and composition of the invention are highly specific and provide a desirably linear relationship of color to enzyme activity. Also, since the invention measures the transaminase activity by the glutamate formed during the incubation, the invention permits the use of pure aqueous standard solutions of glutamate, and eliminates the necessity for using control sera having a known enzyme activity.

The reagent-substrate composition includes transaminase substrate components, i.e., α-ketoglutarate and a substrate amino acid; color reaction components, i.e., the tetrazolium dye and an electron carrier such as the enzyme diaphorase or PMS; and coupling reaction components-GlDH and NAD- in an aqueous solution buffered to a pH at which the transamination can proceed readily. More particularly, the reagent-substrate comprises the substrate, color reaction and coupling reaction components in amounts sufficient to form a measurable color indicative of transaminase activity on incubation with a glutamic transaminase. The reagent-substrate composition is further characterized in that it is essentially free of ammonia or ammonium ions.

The composition of the invention can be prepared by mixing the ingredients in any convenient oreder or fashion. As with any diagnostic reagent composition, ingredients of high purity and quality should be employed. The composition can contain minor amounts of other ingredients in addition to the components mentioned above. For example, surfactants, chelating agents (such as ethylenediamine tetraacetic acid or EDTA) or enzyme activators, such as adenosine diphosphate (ADP) may be employed. In general, a minor amount of a surfactant such as a polyoxyethylene (23) lauryl ether surfactant is desirable. From about 0.01 to 0.05 moles of ADP per liter is also generally desirable. The identity of the substrate amino acid determines the specificity of the composition and method for as particular transaminase. Accordingly, the substrate amino acid can be selected to make the determination specific for GPT in the presence of GOT (by using L-alanine) or for determining total GOT and GPT activity if desired ( by employing both L-aspartate and L-alanine together).

For a GPT determination the L-alanine can be employed as L-alanine or as the racemic mixtures DL-alanine. In the latter case the D-alanine is essentially inert in the determination, and serves only as a diluent. In GOT determinations, D-aspartate has been found to inhibit the GOT transamination reaction. For GOT determinations, L-aspartate rather than its optical isomer, D-aspartate, or racemic mixtures should be employed.

The glutamate dehydrogenase is conveniently employed as a suspension in glycerol. Both the GlDH and the diaphorase should be essentially free of ammonium salts which may frequently be associated with many enzyme preparations.

The tetrazolium dye ingredient can be any tetrazolium salt dye which forms a colored product in electron carrier catalyzed NADH reduction and which does not react detrimentally with the other ingredients or with other materials present during the transamination reaction INT, TNBT (tetranitro-blue tetrazolium), NBT (nitroblue-tetrazolium), NT (neotetrazolium) and BT (blue tetrazolium) all give measurable color in the method of the invention. However, INT gives an unexpected, more intense color than other tetrazolium salt dyes, and is also more soluble than most tetrazolium salts in the test mixture. Accordingly, INT is the preferred tetrazolium dye.

The reagent-substrate composition should be essentially free of ammonia as ammonium ions. It has been found that the presence of minor amounts of ammonium salts, such as may be present either as impurities or as suspending agents or carriers for one or more ingredients, or as may be present in some buffer systems, can severely inhibit the overall progress of the determination. The ingredients should be selected and employed to provide an ammonium ion concentration of less than about 0.001 molar in the ultimate mixture (e.g. from zero or below the limits of detection to about 0.005 molar). The ammonium ion concentration is preferably below 0.001 molar. Ammonium ion from serum does not adversely affect the determination, either at normal serum levels or at levels ten or twenty times normal.

PROPORTIONS OF INGREDIENTS

The reagent - substrate composition can contain the following ingredients in the following proportions:

| Substrate | $\alpha$Ketoglutarate 0.0005 – 0.0012 moles |
| --- | --- |
| | Substrate amino acid 0.01 – 0.5 moles |
| Color Reagent | Tetrazolium dye 0.0005 – 0.005 moles |
| | Electron carrier, Diaphorase (or equivalent, e.g. PMS 0.0001 – 0.0002 moles) 100 – 3200 International Units |
| Coupling Reagents | GlDH 2000 – 40000 International Units |
| | NAD 0.001 – 0.01 moles |
| | Surfactant 1 – 10 grams |
| | Aqueous phosphate buffer (pH 7.2 – 8.5; molarity 0.01 – 1) q.s. to one liter |

A preferred composition contains the components as follows:

| α-Ketoglutarate | 0.0005 – 0.0075 moles |
| --- | --- |
| Substrate amino acid | 0.01 – 0.5 moles |
| INT | 0.0005 – 0.005 moles |
| Diaphorase | 250 – 2000 I.U. |
| GlDH | 2000 – 40000 I.U. |
| NAD | 0.002 – 0.004 moles |
| Surfactant | about 5 grams |
| Aqueous Phosphate buffer (pH Molarity 0.01 – 0.10) 8.0 – 8.2 | q.s. to one liter |

In a specific application for determination of a specific glutamic transaminase such as GOT or GPT, the preferred amount of substrate amino acid will vary, depending on the amino acid employed. For GPT determinations, the amino acid is L-alanine, preferably present in ammounts of from about 0.02 to 0.4 moles per liter of the reagent substrate composition. For GOT determinations, the substrate amine is L-aspartate, and is preferably present in concentrations from about 0.01 to about 0.16 moles per liter.

In the method of the invention, the substrate components, color reaction components and coupling reaction components are mixed with a minor amount of a specimen to be analyzed for transaminase activity; the resulting mixture is incubated under conditions of pH and temperature conducive to the enzyme-catalyzed transamination for a predetermined bried period of time, after which the depth of the resulting color is measured. The mixing is conveniently carried out by mixing a specimen, such as serum, plasma, tissue extracts, enzyme preparations or the like, directly with an aqueous composition of the invention. The relative amounts of specimen and substratereagent composition can vary somewhat depending upon factors such as known or expected concentration of enzyme in the specimen, concentration of ingredients in the composition, etc. In a convenient procedure, about 0.02 to about 0.5 parts by volume of specimen is employed per part by volume of composition.

The incubation pH can range from 7.2 to as high as 9.0. For best results the pH should be in the range of pH 7.9 to pH 8.3, and is preferably controlled by including a buffer in the substrate-reagent composition. The incubation should be carried out at a temperature of from about 20°–40°, and is preferably carried out at about 37° C. In a preferred procedure, the composition is preheated to the incubation temperature prior to addition of the specimen.

The incubation time prior to measuring color is critical to the successful practice of the invention. The incubation time can be controlled by conventional procedures, using known equipment, such as continuous flow analyzers or recording spectrophotometers. The incubation can be terminated readily by addition of acid, conveniently by diluting the mixture with aqueous hydrochloric acid to reduce the pH to pH 0.1 to pH 4.5 after which the color remains stable for 30 minutes or more during which time the absorbance can be measured. The predetermined incubation time should be sufficient for the production of a measurable color, and should be less than about 15 minutes. With longer incubation times, such as 20 or 30 minutes, not only is the advantage of a rapid determination eroded, but the sensitivity and linearity of the determination can be detrimentally affected.

In a preferred procedure, incubation at pH 8.0 – 8.2 is carried out at 35°–40° C. for from about 5 to about 15 minutes, and is terminated by addition of aqueous hydrochloric acid. The depth of color formed is measured by measuring absorbance in a colorimeter or spectrophotometer with light having a wavelength of about 450–550 nanometers. The enzyme activity is determined by comparison to absorbance measurements obtained with control sera, standard solutions containing known amounts of glutamate, standard curves or the like.

The following examples illustrate the invention:

EXAMPLE 1

A reagent substrate composition is prepared to contain the following ingredients in aqueous ammonia-free solution, in the following proportions.

| INT | $8 \times 10^{-4}$ | molar |
|---|---|---|
| NAD | $21.4 \times 10^{-4}$ | molar |
| L-alanine | 0.1 | molar |
| α-ketoglutarate | $1 \times 10^{-3}$ | molar |
| EDTA | $0.2 \times 10^{-4}$ | molar |
| Surfactant (Brij – 35) | 5 | grams/liter |
| GlDH (as glycerol suspension) | 2.7 | I.U./ml. |
| Diaphorase | 0.5 | I.U./ml. |
| Phosphate Buffer pH 8.1 ($KH_2PO_4$ and NaOH) | 0.8 | molar |

One milliliter of the composition is transferred to each of a series of vials and mixed well. The vials are employed for determination of GPT in a specimen control serum, or dilutions of the identical control serum with aqueous 0.85 percent saline. Each vial is preheated in a heating block at 37° C. for 5 minutes before addition of the specimen.

100 Microliters of the appropriate fluid (control serum or a dilution thereof) are added to each of five vials, and the contents are mixed. 100 Microliters of aqueous 0.85 percent saline are mixed with the contents of an additional vial to serve as a blank. After 10 minutes incubation at a temperature of about 37° C., the incubation is terminated by diluting the contents of each vial with 2 milliliters of aqueous hydrochloric acid (about 0.1 normal).

The intensity of the color in each vital is then measured by measuring absorbance at 500 nanometers using a photoelectric colorimeter. (The instrument is previously adjusted to zero absorbance using distilled water). An identical series of control serum and serum dilutions are also analyzed using a commercially available ultraviolet enzyme determination method. Comparison of a plot of the results versus concentration of serum in the specimens shows excellent linearity and good correspondence of the colorimetric determination with the ultraviolet determination.

EXAMPLE 2

A reagent substrate composition is prepared to contain $1.6 \times 10^{-4}$ molar PMS, $8 \times 10^{-4}$ molar INT, $21.4 \times 10^{-4}$ molar NAD, $1000 \times 10^{-4}$ molar L-alanine, $10 \times 10^{-4}$ molar α-ketoglutarate, $0.2 \times 10^{-4}$ molar EDTA and 2700 I.U. per liter GlDH in phosphate buffer surfactant solution which also contains one gram bovine serum albumin per liter. The composition is tested in a procedure similar to that described in Example 1, using varying known amounts of aqueous glutamate standard solution to evaluate linearity of the substrate and method in the presence of the added protein. A plot of absorbance readings versus concentration of added glutamate (ten determinations from $0.4 \times 10^{-4}$ to $4 \times 10^{-4}$ molar glutamate in the test mixture) shows excellent linearity.

EXAMPLE 3

A GOT reagent-substrate composition is prepared to contain the following ingredients in the concentrations set out below:

| α-Ketoglutarate | 0.001 molar |
|---|---|
| L-aspartic acid | 0.020 molar |
| INT | 0.0008 molar |
| NAD | 0.003 molar |
| Diaphorase | 500 I.U./liter |
| GlDH | 8,000 I.U./liter |
| Phosphate buffer (pH 8.1) | 0.05 molar |

A GPT reagent-substrate composition is prepared to contain the same ingredients in the same concentrations, except that the GPT composition contains 0.05 molar L-alanine and no aspartic acid.

The compositions are separately dispensed into separate vials, one milliliter per vial. They are employed in determinations of GOT and GPT respectively. In such procedure, the compositions are preheated in a 37° C. heating block for 10 minutes, then mixed with 0.1 milliliter of a serum sample, control serum, distilled water blank, or aqueous glutamic acid standard solution. The mixtures are incubated for 10 minutes at 37° C., then mixed with 2.0 milliliters of 0.1 normal hydrochloric acid to terminate the enzymatic reactions. The resulting color is measured in a colorimeter with light having a wavelength of about 500 nanometers.

EXAMPLE 4

A reagent-substrate composition is prepared to contain 0.05 molar L-aspartate, 0.0075 molar α-ketoglutarate, 0.0028 molar NAD, 0.002 molar INT, 800 I.U. diaphorase and 4000 I.U. GlDH per liter in 0.05 molar phosphate buffer (pH about 8.1) containing 0.5 percent surfactant (Brij-35). The composition is employed to determine GOT activity on aliquots of 42 human serum samples using substantially the same procedure described in Examples 1 and 3. GOT activity on aliquots of the same serum samples is also determined by the method of Henry, Chiamori, Golub, and Berkman, Am. J. Clin. Path. 34, 381 (1960). Statistical analysis of the results indicates good correlation between the methods.

In a similar procedure, a GPT composition and method similar to that of Example 3 is tested for correlation with the above reference method, using 34 serum samples, with excellent correlation between the two methods.

In a particularly useful embodiment, the reagent substrate composition can be prepared in the form of separate compositions, one of which contains the substrate amino acid, and the other of which contains the color reagent and coupling ingredients. The α-ketoglutarate can be in either composition or can be added separately. The separate reagent composition, containing the color reagent and coupling ingredients in the ratios set out above, can be used directly for quantitative glutamate determinations.

In determinations of enzymatic activity, the separate use of components is convenientyl employed to make use of the biological fluid specimens as individual blanks. In such a procedure, the color reagent and coupling reagents are incubated with the specimen for a time sufficient for the absorbance of the resulting mixture to reach a stable, constant value. This time is generally brief, about one to three minutes. During this incubation, small quantities of glutamate or substrate amines present in the specimen are consumed, and the resulting stable absorbance value can be used as a blank value, or baseline for comparison. The remaining ingredients are then added to form the ultimate substrate-reagent composition, and the incubation is continued, absorbance is measured and compared to the blank, enzyme activity is determined as described above. This embodiment is further illustrated in the following example.

EXAMPLE 5

Reagent-substrate compositions are prepared for separate determinations of GOT and GPT. The color reagent-coupling ingredient composition is prepared in concentrate form so that dilution of two milliliters thereof with one milliliter of the appropriate substrate will provide an ultimate composition of 6 millimolar NAD, 0.8 millimolar INT, 0.02 millimolar ethylene diamine tetraacetic acid, 10 millimolar ADP, 50 I.U. diaphorase per liter and 8000 I.U. GlDH per liter in pH 8.0, 0.1 molar aqueous phosphate buffer. The GOT and GPT substrate compositions are separately prepared in concentrated form to provide ultimate mixtures, containing 4 millimolar α-ketoglutarate in 8, 0.1 molar phosphate buffer and 60 millimolar L-aspartic acid (in the case of the GOT substrate) or 100 millimolar D-L-alanine (in the case of the GPT substrate).

The compositions are used to determine both GOT and GPT in 43 human serum specimens, and the results are compared to the results obtained in analyzing aliquots of the same 43 sera by the method of Henry et al. referred to in Example 4. In the determinations, two milliliters of the color reagent-coupling reagent concentrate are warmed to 37° C. and mixed with 100 microliters of the serum specimen. The mixture is then incubated for 2 minutes at 37° C., then absorbance (at about 500 nanometers) is measured and recorded as a serum blank value. One milliliter of the appropriate GOT or GPT substrate concentrate is then added and mixed. The resulting ultimate mixture is incubated at 37° C. for 10 minutes. Absorbance is measured and recorded after this 10 minute period, the timing being controlled so that termination of incubation by acid is unnecessary. Enzyme activity is calculated from the absorbance difference between the incubated completed mixture and the blank by comparison to the absorbance measurement obtained with a glutamate standard solution.

In measurement of GOT, the results correlate well with results obtained in the reference method, with a correlation coefficient of 0.9932, and a linear correlation plot having a slope of 0.9547. The relationship of absorbance results to GOT activity is found to be linear to about 300 I.U. GOT per milliliter of serum. Excellent correlation is also obtained in the GPT determination, with a correlation coefficient of 0.9937 and a plot having a slope of 1.034. The results obtained indicate excellent linearity to about 200 I.U. GPT per milliliter of serum.

It will be apparent that various modifications in the above procedure can be made, for example, by including the1 α-ketoglutarate in the color reagent-coupling ingredient concentrate or adding it separately, or by varying the concentration of ingredients in the concentrates while maintaining the proportions of ingredients relative to each other.

What is claimed is:

1. In a method for determination of glutamate and glutamic transaminases comprising forming a mixture of a specimen to be analyzed with oxidized nicotinamide adenine dinucleotide; a transaminase substrate, a substrate amino acid, glutamate dehydrogenase, a tetrazolium dye adapted to form a colored reaction product on reaction with reduced nicotinamide adenine dinucleotide, and an electron carrier in a concentration sufficient to catalyze said reaction of the tetrazolium dye and reduced nicotinamide adenine dinucleotide, incubating the mixture under conditions of pH and temperature conducive to formation of a measurable color therein, and measuring the color produced after a predetermined incubation time, the improvement wherein:

a. the specimen is mixed with a reagent substrate solution which has an ammonium ion concentration of less than about 0.001 molar; and which contains from about 0.0005 to about 0.005 moles of tetrazolium dye per liter, from about 2000 to about 40,000 International Units of glutamate dehydrogenase per liter; and from about 0.002 to about 0.004 moles oxidized nicotinamide adenine dinucleotide per liter, from about 250 to about 2000 International Units of diaphorase per liter, α-ketoglutarate in a concentration of from about 0.0005 to about 0.0012 moles per liter, and a substrate amino acid selected from the group consisting of L-alanine and L-aspartate in a concentration of from about 0.01 to about 0.5 moles per liter, and an aqueous buffer adapted to maintain a pH of from about 8.0 to about 8.2 of the substrate reagent solution; and wherein the color is measured after incubation of the resulting mixture of specimen and reagent substrate solution solution at a temperature of from about 35° to about 40° C., and a pH of from about 7.9 to about 8.3 for a predetermined time sufficient to develop a measurable color therein and less than about 15 minutes.

2. The method of claim 1 wherein the substrate amino acid is L-alanine and the concentration thereof is from about 0.02 to about 0.4 moles per liter.

3. The method of claim 1 wherein the substrate amino acid is L-aspartate and the concentration thereof is from about 0.01 to about 0.16 moles per liter.

* * * * *

UNITED STATES PATENT AND TRADEMARK OFFICE
CERTIFICATE OF CORRECTION

Page 1 of 2

PATENT NO. : 4,024,021
DATED : May 17, 1977
INVENTOR(S) : William S. Stavropoulos, et al.

It is certified that error appears in the above-identified patent and that said Letters Patent are hereby corrected as shown below:

First page, [56] under title OTHER PUBLICATIONS, second line, "Glutamic-Pyluvic" should read --Glutamic-Pyruvic--.

Column 1, between lines 1 - 5, after title but before paragraph, put in --CROSS-REFERENCE TO RELATED APPLICATION--.

Column 1, line 32, "aqueousl" should read --aqueous--.

Column 1, line 44, should read --NADH + INT $\xrightarrow{PMS}$ NAD + INT formazan--.

Column 2, line 14, "the" should read --be--.

Column 2, line 54, "oreder" should read --order--.

Column 2, line 68, "as" should read --a--.

Column 3, line 16, "ClDH" should read --GlDH--.

Column 3, line 21, "in electron" should read --in an electron--.

Column 3, line 55, "Substrate αKetoglutarate 0.0005 - 0.0012 moles" should read --Substrate α-Ketoglutarate 0.0005 - 0.0012 moles--.

Column 4, line 12, "ammounts" should read --amounts--.

Column 4, line 23, "bried" should read --brief--.

Column 4, line 29, "substratereagent" should read --substrate-reagent--.

UNITED STATES PATENT AND TRADEMARK OFFICE
CERTIFICATE OF CORRECTION

PATENT NO. : 4,024,021
DATED : May 17, 1977
INVENTOR(S) : William S. Stavropoulos, et al.

It is certified that error appears in the above-identified patent and that said Letters Patent are hereby corrected as shown below:

Column 4, line 41, "20°-40°," should read --25°-40°,--.

Column 5, line 40, "vital" should read --vial--.

Column 6, line 64, "convenientyl" should read --conveniently--.

Column 7, line 27, "in 8," should read --in pH 8,--.

Column 8, line 7, "thel" should read --the--.

Signed and Sealed this

Eighth Day of November 1977

[SEAL]

Attest:

RUTH C. MASON
Attesting Officer

LUTRELLE F. PARKER
Acting Commissioner of Patents and Trademarks